(12) United States Patent
Chen et al.

(10) Patent No.: US 6,309,878 B1
(45) Date of Patent: *Oct. 30, 2001

(54) GLUCOSE-INDUCIBLE RECOMBINANT VIRAL VECTOR

(75) Inventors: Ruihuan Chen, New York, NY (US); Bruno Doiron, Champs sur Marne; Axel Kahn, Paris, both of (FR)

(73) Assignee: Institut National de la Sante et de la Recherche Medicale, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/945,140

(22) PCT Filed: Apr. 12, 1996

(86) PCT No.: PCT/FR96/00560

§ 371 Date: Dec. 17, 1997

§ 102(e) Date: Dec. 17, 1997

(87) PCT Pub. No.: WO96/32489

PCT Pub. Date: Oct. 17, 1996

(30) Foreign Application Priority Data

Apr. 14, 1995 (FR) .................................................. 95 04558

(51) Int. Cl.[7] .............................. C12N 5/10; C12N 15/63; C12N 15/86
(52) U.S. Cl. ........................ 435/325; 435/320.1; 435/366; 435/370
(58) Field of Search ................................. 435/320.1, 325, 435/366, 370; 514/44; 424/93.2, 93.21

(56) References Cited

FOREIGN PATENT DOCUMENTS

| 92/21750 | 12/1992 | (WO) . |
| 93/03769 | 3/1993 | (WO) . |
| 94/21806 | 9/1994 | (WO) . |
| 95/00644 | 1/1995 | (WO) . |

OTHER PUBLICATIONS

Orkin et al, Report and Recommendations of the Panel to Assess the NIH Investment in Research on Gene Therapy, released by NIH, 41 unnumbered pages, Dec. 7, 1995.*
Verma et al, Nature, vol. 389, pp. 239–242, Sep. 18, 1997.*
Doiron et al., Respective Roles of Glucose, Fructose, and Insulin in the Regulation of the Liver–Specific Pyruvate Kinase Gene Promoter, Journal of Biological Chemistry 269(14) 10213–10216 (1994).
Chen et al., Glucose responsibeness of a reporter gene transduced into hepatocytic cells using a retroviral vector, FEBS Letters 365 223–226 (1995).
Bergot et al., Cis–regulation of the L–type pyruvate kinase gene promoter by glucose, insulin and cyclic AMP, Nucleic Acid Research 20(8) 1871–1878 (1992).
Sabourin et al., An Intronic Enhancer Essential for Tissue–specific Expression of the Aldolase B Transgenes, Journal of Biological 271(7) 3469–3473 (1996.

* cited by examiner

Primary Examiner—Terry McKelvey
(74) Attorney, Agent, or Firm—Finnegan, Henderson, Farabow, Garrett & Dunner, LLP

(57) ABSTRACT

A defective recombinant virus including at least one heterologous gene controlled by a glucose-inducible expression signal, a pharmaceutical composition containing same, and cells transformed using said vector, are disclosed.

24 Claims, 7 Drawing Sheets pHSG/PK-CAT:

pHSG/AL-PK-CAT:

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 194 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GATCCAGCAG CATGGGCGCA CGGGGCACTC CCGTGGTTCC TGGACTCTGG CCCCCAGTGT      60

ACAAGGCTTC CGTTGGCAAG AGAGATGCTA GCTGGTTATA CTTTAACCAG GACTCATCTC     120

ATCTGAGCCA GGCCCCATCC CACTGACAAA GGCGCAGTAT AAAGCAGACC CACAGACACA     180

GCAGGTAAGC AACG                                                      194
```

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:2:

GCGCACGGGG CACTCCCGTG GTTC                                              24

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:3:

CTGGACTCTG GCCCCCAGT                                                    19

(2) INFORMATION FOR SEQ ID NO:4:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GGCTTCCGTT GGCAAGAGAG ATGCTAGCTG GTTATACTTT AACCAGGACT CATCTCATCT       60

GAGCCAGGCC CATCCCACTG ACAAAGGCGC AGTATAAAGC AGACCCACAG ACACAGCAGG      120

TAAGCAACG                                                              129

(2) INFORMATION FOR SEQ ID NO:5:

(i) SEQUENCE CHARACTERISTICS:
        (A) LENGTH: 416 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

TCCTTCTGCC ATGGCCCTGT GGATGCGCCT CCTGCCCCTG CTGGCGCTGC TGGCCCTCTG       60

GGGACCTGAC CCAGCCGCAG CCTTTGTGAA CCAACACCTG TGCGGCTCAC ACCTGGTGGA      120

AGCTCTCTAC CTAGTGTGCG GGAACGAGG CTTCTTCTAC ACACCCAAGA CCCGCCGGGA       180

GGCAGAGGAC CTGCAGGTGG GCAGGTGGA GCTGGGCGGG GGCCCTGGTG CAGGCAGCCT       240

GCAGCCCTTG GCCCTGGAGG GGTCCCTGCA GAAGCGTGGC ATTGTGGAAC AATGCTGTAC      300

CAGCATCTGC TCCCTCTACC AGCTGGAGAA CTACTGCAAC TAGACGCAGC CGCAGGCAG       360

CCCCCCACCC GCCGCCTCCT GCACCGAGAG AGATGGAATA AAGCCCTTGA ACCAGC          416

(2) INFORMATION FOR SEQ ID NO:6:

(i) SEQUENCE CHARACTERISTICS:
        (A) LENGTH: 464 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

AGGCCTCCAC ACTCTATTGC ACTCTGCAGA AGTAACACTA GAGTGACCTT TCTTTAGATT      60

TAGAAAGACT AACACATAAT ATATTGCTGT AATTTCTTTT GTAGTTTTTT AAGTAGGACA     120

ATAAATATTT ATTACAGATT TCTCTGGAAG TTTTTCATTT GATAATTAAT GAAAATTTTC     180

CATCATACTT GTAAAAATGA AGTGACTTGG GACCTTAGAA ATCAGAAGTT TAAAGGAGTA     240

AAGTTCATTA TTGTTAAGTA TTCCAGGCTG TGTTCTGTCT CCCAGTGACA AACATTGACC     300

TGTGACTCTG TTTTATGATT AACTGAGGGG CAAAATTTGT GCTGATGTGG TACAGACCTT     360

TAGTCCCTTT GTAGAAGTTT AACTTCCTGT AAACAGGACG AGTTTGACTT GACTTTTCCC     420

TGTAATTCTT GTTGAGTTGG CATACCCAGA ATGGAGCAAA TGGC                     464

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:7:

ACTCAAATGC CCAATGAAGT C                                                21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:8:

TCAACGGTGG TATATCCAGA T                                                21

(2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:9:

GCGCACGGGG CA                                                          12

(2) INFORMATION FOR SEQ ID NO:10:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:10:

AACCACGGGA GT                                                          12

GLUCOSE-INDUCIBLE RECOMBINANT VIRAL VECTOR

This application is a §371 filing of PCT/FR96/00560, filed Apr. 12, 1996.

The present invention relates to recombinant vectors of viral origin, to the preparation of these vectors, to pharmaceutical compositions containing them and to their therapeutic use, in particular in gene therapy, and more especially for the treatment and/or prevention of pathologies associated with a hyperglycaemia.

Gene therapy consists in correcting a deficiency or an abnormality (mutation, aberrant expression, and the like) by introducing genetic information into the cell or organ affected. Traditionally, this genetic information may be introduced either in vitro into a cell extracted from the organ, the modified cell then being reintroduced into the body or directly in vivo into the appropriate tissue. Different techniques have been described for the introduction of this genetic information, among them various techniques of transfection involving complexes of DNA and DEAE-dextran (Pagano et al., J. Virol. 1 (1967) 891), of DNA and nuclear proteins (Kaneda et al., Science 243 (1989) 375) and of DNA and lipids (Felgner et al., PNAS 84 (1987) 7413), the use of liposomes (Fraley et al., J. Biol. Chem. 255 (1980) 10431), and the like.

More recently, the use of viruses as vectors for gene transfer has been seen to be a promising alternative to these physical transfection techniques. In this connection, different viruses have been tested for their capacity to infect certain cell populations. In particular, retroviruses (RSV, HMS, MMS, and the like), the HSV virus, adeno-associated viruses and adeno viruses [lacuna].

The present invention relates more especially to the development of new viral vectors which are, in particular, of special interest for the treatment of pathologies associated with hyperglycaemia such as diabetes.

Sugar diabetes is a syndrome, usually chronic, whose most characteristic symptom is a hyperglycaemia causing, in the absence of an elevation of the renal glucose threshold, a glycosuria. Its main cause is an absolute or relative deficiency of insulin, giving rise to abnormalities not only of carbohydrate metabolism but also of those of proteins and fats.

Diabetes is generally treated by administration of insulin, a treatment which proves very restricting for the patient.

The objective of the present invention is specifically to provide a novel viral vector enabling this disorganization of glucose metabolism to be compensated in the body via the restoration in a controlled manner of an appropriate in vivo insulin concentration.

Glucose is known to be a factor regulating gene transcription in the majority of living organisms. It has been demonstrated, in particular, that glucose is capable of stimulating the transcription of genes coding for glycolytic and lipogenic enzymes in hepatocytes and adipocytes, such as, for example, the gene for type L pyruvate kinase, a tissue-specific glycolytic enzyme which plays a decisive part in the regulation of glycolysis and gluconeogenesis in the liver. The expression of the L-PK protein in the liver is under nutritional and hormonal control. It is induced by a glucose-rich diet and, on the contrary, inhibited by deprivation and in diabetics. Thus, it has been demonstrated that the expression of its gene is positively regulated by the glucose/insulin system and negatively by glucagon via its second messenger cyclic AMP (A. Kahn; J. Bio. Chem. 264, (1989), 11584–11590).

Recently, the Applicant has characterized different binding sites (elements L1 to L4) for transcription factors, and especially a glucose/insulin response element, or "GIRE", in the region upstream of the promoter of the gene for this L-PK enzyme (A. Kahn et al., J. Mol. Biol. 209, (1989), 205–219). Thus he identified, in the 3' to 5' direction starting from the TATA box, the L1 element, a binding site for hepatocyte nuclear factor 1 (HNF1), the L2 element, a binding site for nuclear factor 1 (NF1), the L3 element, a binding site for hepatocyte nuclear factor 4 (HNF4) and the L4 element, a binding site for the major late transcriptional factor (MLTF)/USF (see FIG. 1), respectively. The specific element for glucose/insulin response has been precisely localized in the gene coding for L-PK, in the form of a perfect palindrome between nucleotides −168 and −144 from the cap site, that is to say in the L4 element (see FIG. 2). This GIRE has been shown to be capable of conferring a transcriptional response to glucose on a minimal L-PK promoter consisting of the TATA box and the L1 element.

Unexpectedly, the Applicant demonstrated that it was possible to upgrade the capacity of this GIRE element to respond to glucose in a viral context in order to modulate the expression of a protein of interest in gene therapy.

More specifically, the present invention relates to a defective recombinant virus comprising at least one heterologous gene under the control of an expression signal which is inducible by glucose or one of its analogues.

Glucose analogue is understood to cover any compound displaying structural homologies with glucose and which is capable of inducing the activation of the expression signal. As analogues capable of being used according to the present invention, fructose, galactose, sucrose, lactose and all sugars capable of being hydrolysed to these substances may be mentioned in particular.

For the purposes of the present invention, an expression signal which is inducible with glucose covers any expression signal sequence whose activation, which conditions the subsequent transcription of the associated heterologous gene, is essentially induced in the presence of glucose or one its analogues.

More especially, the virus in question is a defective recombinant virus in which the expression of at least one heterologous gene is placed under the control of an expression signal derived wholly or partially from the promoter of the gene coding for type L pyruvate kinase, L-PK. More specifically, this expression signal is derived wholly or partially from the fragment consisting of the 183 bp located at the 5' end of the coding frame of the gene coding for L-PK.

Preferably, the expression signal according is to the invention comprises all or part of the sequence SEQ ID NO: 1.

According to a preferred embodiment, this expression signal comprises at least all or part of the L4 element of this promoter.

The L4 element is preferably represented by all or part of the sequence SEQ ID NO: 2, of a sequence hybridizing with all or part of the latter or of a sequence which is derived therefrom, and capable of interacting with the factor MLTF/USF.

For the purposes of the present invention, derivative is understood to mean any sequence obtained by one or more modifications and which retains at least one of the biological properties of the original sequence, and in particular its capacity to interact with its specific binding factor or factors, in the present case consisting of the factor MLTF/USF. Modification is understood to mean any mutation, substitution, deletion, addition or modification of a genetic and/or chemical nature. These modifications may be carried out by the techniques known to a person skilled in the art.

In a variant of the invention, the L4 element is repeated in the form of 4 successive oligomers in the expression signal.

According to a preferred embodiment of the invention, the expression signal comprises, besides the L4 element, all or part of the L3 element of the promoter of the gene coding for L-PK.

It has, in effect, been mounted that this L3 element contributes to an improved efficacy of the L4 element (A. Kahn et al., Nucleic Acids Research 20, (1992), No. 8 p. 1871). The L3 element is preferably represented wholly or partially by the sequence SEQ ID NO: 3, a sequence hydridizing with all or part of the latter or of a sequence which is derived therefrom, capable of interacting with the factor HNF4.

According to a preferred embodiment of the invention, the expression signal comprises the L4 element of the promoter of the gene coding for L-PK, fused upstream of the L3 element of this same promoter. It is then designated L4-L3. More preferentially, the expression signal according to the invention comprises 4 successive L4-L3 oligomers.

This expression signal comprises, in addition, a so-called minimal promoter.

For the purposes of the present invention, minimal promoter denotes any promoter sequence which, on its own, is not capable of providing effectively for the transcription of the heterologous sequence which is associated with it. The activity of such a promoter proves to be totally dependent on the activation of the element responding to glucose. In fact, this minimal promoter has, most of all, the function of guiding the transcription. From this standpoint, it is preferably located upstream of the heterologous sequence so as to form a continuous nucleotide sequence therewith.

It is possible to employ, according to the invention, a minimal promoter derived from a conventional promoter, such as, for example, those activating the transcription of a gene of the thymidine kinase, chloramphenicol acetyltransferase, β-galactosidase or luciferase type or, in particular, derived from the promoter of the gene coding for type L pyruvate kinase. This minimal promoter may also be derived from human CMV. Where appropriate, such a promoter may be rendered minimal by the expedient of one or more genetic mutations which make it incapable of providing on its own for the transcription of the heterologous gene.

According to the same principle, the minimal promoter may be derived from the promoter naturally responsible for the expression of the heterologous gene in question.

As a minimal promoter capable of being used according to the invention, the sequence corresponding to the fragment −119 to 11 located at the 5'end of the gene coding for L-PK may be mentioned more especially.

Generally speaking, this minimal promoter is placed upstream of the nucleic acid sequence whose expression it controls, as a substitute or otherwise for its natural promoter. The promoter belonging to the nucleic acid sequence can, in effect, remain present, but in an inactivated form or a form rendered non-functional by different techniques known to a person skilled in the art, and in particular by elimination, deletion and/or addition of one or more bases.

More preferably, the expression signal corresponds wholly or partially to the sequence SEQ ID NO: 4 or one of its derivatives.

Moreover, the promoter region may be modified by adding activating or regulatory sequences (in particular enhancer sequences), which make it possible to increase the strength of the promoter without affecting its inducible character. In particular, with the aim of enhancing the strength of the promoter, we constructed a hybrid vector in which the 183-bp promoter of the PK-L gene is preceded by a 402-bp fragment situated in the first intron of the rat aldolase B gene, from nucleotide 1920 to nucleotide 2321 relative to the site of initiation of transcription (SEQ ID NO: 6 corresponding to nucleotides 1915 to 2379). The results presented in the examples show that this construct increases the expression of a gene by a factor of 5, in response to glucose.

As regards the heterologous nucleic acid sequence placed under the control of the expression signal according to the invention, this contains one or more therapeutic genes whose transfer into a cell, organ or body, and/or expression therein, is sought.

The therapeutic genes which may be transferred in this way are any gene whose transcription and, where appropriate, translation in the target cell generate products having a therapeutic effect.

Such genes can be, in particular, ones coding for proteinaceous products having a therapeutic effect. The proteinaceous product thus encoded can be a protein, a peptide, an amino acid, and the like. This proteinaceous product may be homologous with respect to the target cell (that is to say a product which is normally expressed in the target cell when the latter does not display any pathology). In this case, the expression of a protein makes it possible, for example, to compensate for an insufficient expression in the cell, or the expression of a protein which is inactive or weakly active as a result of a modification, or alternatively to overexpress the said protein. The therapeutic gene may also code for a mutant of a cell protein, having an enhanced stability, a modified activity, and the like. The proteinaceous product may also be heterologous with respect to the target cell. In this case, an expressed protein may, for example, supplement or supply an activity which is deficient in the cell, enabling it to combat a pathology.

Among therapeutic products for the purposes of the present invention, there may be mentioned more especially enzymes, blood derivatives, hormones such as insulin, lymphokines, namely interleukins, interferons, TNF, and the like (FR 92/03120), growth factors, neurotransmitters or their precursors or synthetic enzymes, trophic factors, namely BDNF, CNTF, NGF, IGF, GMF, aFGF, bFGF, NT3, NT5, and the like; apolipoproteins, namely ApoAI, ApoAIV, ApoE, and the like (FR 93/05125), dystrophin or a minidystrophin (FR 91/11947), and the like.

According to a preferred variant of the invention, the heterologous sequence contains at least one gene coding for insulin or an insulin variant. For the purposes of the invention, variant covers, in particular, the different maturation forms of insulin, such as, for example, proinsulin (Vollenweider et al., J. Biol. Chem. 267, (1992) 14629–14636 and Groskreutz et al., J. Biol. Chem. 269, (1994), 6241–6245).

More preferably, the gene coding for insulin and present in a vector according to the invention comprises all or part of the sequence SEQ ID NO: 5.

The vectors of the invention may be prepared from different types of virus. Preferably, vectors derived from adenoviruses or from retroviruses are used.

The viruses according to the invention are defective, that is to say they are incapable of replicating autonomously in the target cell. Generally, the genome of the defective viruses used in the context of the present invention hence lacks at least the sequences necessary for replication of the said virus in the infected cell. These regions may be either removed (wholly or partially), or rendered non-functional, or substituted by other sequences, and in particular by the DNA sequence coding for the gene of interest, such as, for example, the insulin gene. Preferably, the defective virus nevertheless retains the sequences of its genome which are necessary for encapsidation of the viral particles.

As regards adenoviruses more especially, different serotypes whose structure and properties vary somewhat have been characterized. Among these serotypes, it is preferable to use, in the context of the present invention, human adenoviruses type 2 or 5 (Ad 2 or Ad 5) or adenoviruses of animal origin (see Application FR 93/05954). Among adenoviruses of animal origin which can be used in the context of the present invention, adenoviruses of canine, bovine, murine (for example: Mav1, Beard et al., Virology 75 (1990) 81), ovine, porcine, avian or alternatively simian (for example: SAV) origin may be mentioned. Preferably, the adenovirus of animal origin is a canine adenovirus, more especially a CAV2 adenovirus [strain Manhattan or A26/61 (ATCC VR-800) for example]. Preferably, adenoviruses of human or canine or mixed origin are used in the context of the invention.

Preferably, the defective adenoviruses of the invention comprise the ITRs, a sequence permitting encapsidation and the sequence coding for the protein of therapeutic interest. Still more preferably, in the genome of the adenoviruses of the invention, the E1 gene and at least one of the genes E2, E4 and L1–L5 are non-functional. The viral gene in question may be rendered non-functional by any technique known to a person skilled in the art, and in particular by total elimination, substitution, partial deletion or addition of one or more bases in the gene or genes in question. Such modifications may be obtained in vitro (on isolated DNA) or in situ, for example by means of genetic engineering techniques, or alternatively by treatment by means of mutagenic agents. The defective recombinant adenoviruses according to the invention may be prepared by any technique known to a person skilled in the art (Levrero et al., Gene 101 (1991) 195, EP 185 573; Graham, EMBO J. 3 (1984) 2917).

As regards retroviruses, the construction of recombinant vectors has been amply described in the literature: see, in particular, Breakfield et al., New Biologist 3 (1991) 203; EP 453242, EP 178220, Bernstein et al., Genet. Eng. 7 (1985) 235; McCormick, BioTechnology 3 (1985) 689, and the like. In particular, retroviruses are integrative viruses which selectively infect dividing cells. The genome of retroviruses essentially comprises two LTRs, an encapsidation sequence and three coding regions (gag, pol and env). In the recombinant vectors derived from retroviruses, the gag, pol and env genes are generally deleted wholly or partially, and replaced by a heterologous nucleic acid sequence of interest. These vectors may be produced from different types of retrovirus, such as, in particular, MoMuLV ("Murine moloney leukaemia virus"; also designated MoMLV), MSV ("Murine moloney sarcoma virus"), HaSV (Harvey sarcoma virus"), SNV ("spleen necrosis virus"), RSV ("Rous sarcoma virus") or alternatively Friend virus.

To construct recombinant retroviruses containing a sequence of interest, a plasmid containing, in particular, the LTRs, the encapsidation sequence and the said sequence of interest is generally constructed, and is then used to transfect a so-called encapsidation cell line capable of supplying in trans the retroviral functions which are deficient in the plasmid. Generally, the encapsidation lines are hence capable of expressing the gag, pol and env genes. Such encapsidation lines have been described in the prior art, and in particular the PA317 line (U.S. Pat. No. 4,861,719), the PsiCRIP line (WO 90/02806) and the GP+envAm-12 line (WO 89/07150). As an example of the line, there may be mentioned, in particular the ψ-2 cell line which originates from the NIH-3T3 line (mouse fibroblast line) by transfection with pMOV-ψ⁻, a plasmid containing the genome of the Moloney murine leukaemia virus (MoMuLV) from which the "ψ" encapsidation sequence is deleted (Mann et al., Cell, (1983), 33, 153–159). Moreover, the recombinant retroviruses can contain modifications in respect of the LTRs to eliminate transcriptional activity, as well as extended encapsidation sequences containing a portion of the gag gene (Bender et al., J. Virol. (1987) 61, 1639). The recombinant retroviruses produced are then purified by standard techniques.

In the particular case of the present invention, the retroviruses may be prepared by transfection of a retroviral plasmid containing the expression signal according to the invention, coupled to the gene coding for the protein of interest, into a transcomplementing cell line which will enable viral particles whose genome codes for the transgene to be produced.

To carry out the present invention, it is most especially advantageous to use a defective recombinant adenovirus or retrovirus, the retrovirus being most especially advantageous for expressing insulin.

By placing, within a vector according to the invention, the expression of the gene coding for insulin under the control of an expression signal controlled by glucose, and by transfecting cells in vivo using this type of vector, these cells are induced to produce insulin under the effect of their physiological content of glucose. These cells become capable of expressing the transgene for insulin in the presence of a physiological and sufficient concentration of glucose.

According to a preferred embodiment of the invention, the transfected cells possess an internal system for detection of glucose, also called glucose sensing machinery, capable of inducing the activation of the expression signal. Some cell types, such as hepatocytes and β cells of the pancreas, are naturally provided with this. The system in question is composed, in particular, of specific enzymes such as the transporter Glut-2-glucose and glucokinase. In the case of cells bereft of this type of sensing machinery, it is perfectly possible to envisage compensating for this artificially. In this particular case, the cells which are to be treated are transfected, either prior to or simultaneously with the injection of the virus according to the invention, by means of genetic constructions, controlling the synthesis of the transporter Glut-2 for the enzyme glucokinase.

The infection of cells such as hepatocytes with recombinant viruses according to the invention may be carried out ex vivo and/or in vivo, rendering the cells thus transfected capable of secreting insulin. Favoured infection sites in the context of the present invention are the natural sites of secretion of insulin, such as the portal vein.

The present invention also relates to mammalian, preferably human cells, and more preferably to hepatocytes and/or pancreatic β cells infected with one or more claimed viruses.

Besides their capacity to induce the expression of insulin in vivo, the vectors according to the invention advantageously enable this secretion to be blocked immediately under the effect of glucagon as a result of classical AMP. In this way, the risk of a hypoglycaemia induced by an excessive secretion of insulin is avoided.

Consequently, the claimed vectors are especially advantageous for controlling in vivo, via a phenomenon of induction with glucose, the production of insulin in a precise region of the body, preferably in a site or it is normally secreted, such as the portal circulation. Cells infected with one or more claimed viruses could thus be inplanted in the liver, spleen, pancreas or intestine.

Thus the present invention describes a novel approach for the treatment, in particular, of insulin-dependent diabetic disorders, consisting in inducing the synthesis of insulin in vivo in response to a physiological content of glucose.

In the particular case where the cells transfected with a vector according to the invention might not possess this physiological content of glucose, initiating the expression of a heterologous gene other than that for insulin for example, the following protocol may be envisaged: the concentration of glucose, or of an analogue having the same influence on the glucose response sequence (L4-L3), would be adjusted therein so as to induce the expression of the protein of interest via the activity of the expression signal according to the invention. It is clear that this concentration is determined as a function of the amount of vectors injected, the nature of the infection site and the desired expression of protein.

As stated above, the present invention also relates to any use of a virus as described above for the preparation of a pharmaceutical composition intended, in particular, for the treatment and/or prevention of disorders associated with a hyperglycaemia.

The present invention also relates to a pharmaceutical composition comprising one or more defective recombinant viruses as described above. These pharmaceutical compositions may be formulated for the purpose of topical, oral, parenteral, intranasal, intravenous, intramuscular, subcutaneous, intraocular, transdermal, and the like, administration. Preferably, the pharmaceutical compositions of the invention contain a pharmaceutically acceptable vehicle for an injectable formulation. Such formulations include, in particular, sterile isotonic solutions, or dry, in particular lyophilized compositions which, on adding physiological saline or sterilized water as appropriate, enable injectable solutions to be made up.

The doses of defective recombinant virus used for the injection may be adapted in accordance with different parameters, and in particular in accordance with the viral vector, the mode of administration used, the pathology in question or the desired treatment period. Generally speaking, the recombinant viruses according to the invention are formulated and administered in the form of doses of between $10^4$ and $10^{14}$ pfu/ml, and preferably $10^6$ to $10^{10}$ pfu/ml. The term pfu (plaque forming unit) corresponds to the infectious power of a solution of virus, and is determined by infecting a suitable cell culture and measuring, generally after 48 hours, the number of plaques of infected cells. The techniques of determination of the pfu titre of a viral solution are well documented in the literature. As regards retroviruses, the compositions according to the invention can contain the producing cells directly, for the purpose of their implantation.

The examples and figures presented below without implied limitation of the present invention will enable other advantages and features of the present invention to be revealed.

General Techniques of Molecular Biology

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, phenol or phenol-chloroform extraction of proteins, ethanol or isopropanol precipitation of DNA in a saline medium, transformation in *Escherichia coli*, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

Plasmids of the pBR322 and pUC type and phages of the M13 series are of commercial origin (Bethesda Research Laboratories).

To carry out ligation, the DNA fragments may be separated according to their size by agarose or acrylamide gel electrophoresis, extracted with phenol or with a phenol-chloroform mixture, precipitated with ethanol and then incubated in the presence of phage T4 DNA ligase (Biolabs) according to the supplier's recommendations.

The filling in of 5' protruding ends may be performed with the Klenow fragment of *E. coli* DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding'ends is performed by a controlled treatment with S1 nuclease.

In vitro site-directed mutagenesis using synthetic oligodeoxynucleotides may be performed according to the method developed by Taylor et al. [Nucleic Acids Res. 13 (1985) 8749–8764]) using the kit distributed by Amersham.

The enzymatic amplification of DNA fragments by the so-called PCR [polymerase-catalysed chain reaction, Saiki R. K. et al., Science 230 (1985) 1350–1354; Mullis K. B. and Faloona F. A., Meth. Enzym. 155 (1987) 335–350] technique may be performed using a "DNA thermal cycler" (Perkin Elmer Cetus) according to the manufacturer's specifications.

Verification of the nucleotide sequences may be performed by the method developed by Sanger et al. [Proc. Natl. Acad. Sci. USA, 74 (1977) 5463–5467] using the kit distributed by Amersham.

EXAMPLE 1

Construction of a Retroviral Vector

Figure 1:
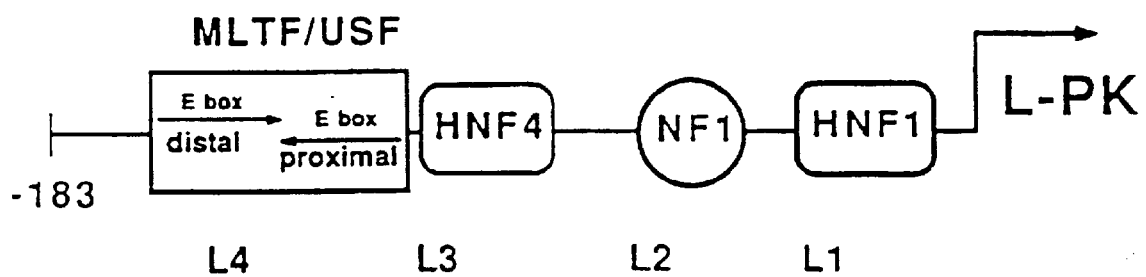
FIG. 1: Diagrammatic representation of the order of succession of the elements L1 to L4 identified in the promoter of the L-PK gene and their respective binding proteins.
Figure 2:
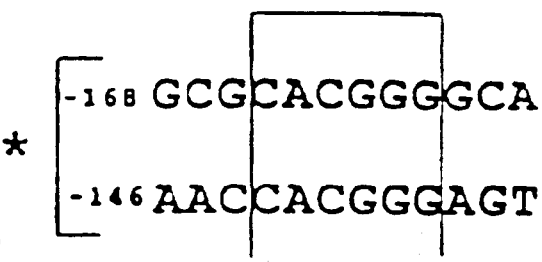
FIG. 2: Representation of the palindrome of the L4 element SEQ. ID NOS: 9 and 10.
Figure 3:
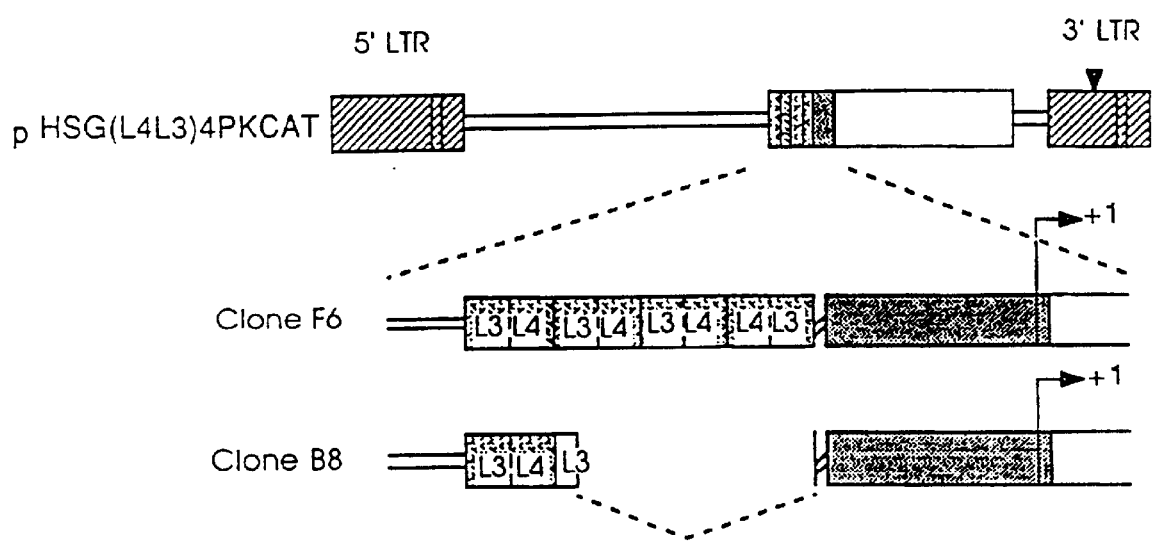
FIG. 3: Partial representation of the retroviral plasmid pHSG(L4L3)4PKCAT and of the clones F6 and B8.

All the plasmids are constructed according to standard DNA cloning techniques. Junctions are verified by DNA sequencing. The construction of plasmid pHSG(L4L3)4-PKCAT, (shown in FIG. 3) contains the MMLV constructive portion of pRSGNeo and the sequence coding for the CAT gene under the control of the promoter of the rat pyruvate kinase type L gene (bp −119 to +11), upstream of which L4L3 fragments oligomerized 4 times (i.e. the GIRE and the adjacent HNF4 binding site) are ligated. The L4L3 fragment, corresponding to the fragment delimited between bp. −172 and −123, upstream of the L-PK transcription initiation site, was obtained by PCR. The polyA signal sequence used is the one present in the LTR of the 3' end of MMLV. Plasmid pHSGNeo (Guild et al. J. Virol. 1988, 62, 3795–3801), a retroviral plasmid derived from MMLV, and the psi-CRIP line, an amphotropic complementary cell line which supplies in trans structural proteins of MMLV, were obtained by Dr A. Weber (Cochin Institute of Molecular Genetics, Paris); plasmid pRSVNeo, in which the aminoglycoside phosphotransferase gene is under the control of the RSV LTR promoter, is used for the cotransfection.

EXAMPLE 2
Cell Culture and Transfection

The mhATIIIF cell line originates from a liver tumour in a transgenic mouse expressing the SV40 early genes under the control of the liver-specific antithrombin III (SV40 ATIII) promoter (Kahn A. et al. Exp. Cell. Res. 200, 175–185). These cells are cultured in a DMEM F12/NUT. MIX. (1:1 vol/vol) nutrient medium with glutamax-1, or DMEM/HamF12 (1:1 vol/vol) nutrient medium (Gibco-BRL) with or without D(+)-glucose (Sigma), supplemented with 1 $\mu$M dexamethasone, 1 $\mu$M triodothyronine, 20 nM human insulin and 5% (vol/vol) of FCS. NIH3T3 and psi-CRIP cells are cultured in: DMEM (5.5 mM glucose, 1.0 mM sodium pyruvate) supplemented with 10% (vol/vol) of newborne calf serum. Ampicillin, streptomycin and glutamine are added to all the media, and cultures are incubated at 37° C. with 5% (vol/vol) $CO_2$. Psi-CRIP sells are cotransfected with plasmids pHSG(L3L4)4-PKCAT and pRSVNeo (the mole ratio of the two plasmids being 10:1) by the cationic liposome method (DOTAP, Boeringer Mannheim) and selected in the presence of G418 (800 $\mu$g/ml). Clones resistant to G418 are separated for the test of production of retroviruses.

EXAMPLE 3
Preparation of the Viral RNA and PCR-RT in One Step

Cell clones resistant to G418 are inoculated into 90-mm wells and cultured to 100 k confluence. The cell culture supernatant is filtered through a membrane possessing 0.22 Am pores, incubated with DNase I (10 $\mu$g/ml) at 37° C. for 30 min and then centrifuged at 65,000 rpm for 20 min at 4° C. The retroviral RNA is extracted and purified from precipitation pellets with proteinase K and a phenol/chloroform mixture, then coprecipitated with tRNA. The sample is dissolved in diethyl pyrocarbonate treated with water and containing 1 mM dithiothreitol (DTT) and 40 U of RNAsin/ 100 $\mu$m, then subjected to a reverse transcriptase and to a PCR in a single step. The two probes used for the amplification are:

5'ACTCAAATGCCCAATGAAGTC3' (SEQ ID NO: 7) corresponding to the Gag region of MMLV (bp 1524 to 1544);

5'TCAACGGTGGTATATCCAGAT3' (SEQ ID No. 8) corresponding to the coding region of the CAT gene (bp 35 to 15 with respect to the translation initiation site).

Reverse transcription from the antisense PCR probe is catalysed by 8U AMV reverse transcriptase (Promega) for 1 hour at 42° C., and the next PCR with Taq25U DNA polymerase is carried out in 35 to 40 cycles. The expected amplified fragment is 440 bp long and contains a portion of the gag gene, 4 L3L4 repeat motifs, the L-PK -119 promoter and the first 69 bp of the CAT gene. If necessary, the RT-PCR fragments are cloned and sequenced.

EXAMPLE 4
Production of Recombinant Retroviruses

The retroviral vectors pHSG(L4L3)4-119PKCAT and pRSVNeo are used to cotransfect psi-CRIP cell lines. 70 G418-resistant clones are analysed. 8 Clones which are positive in RT-PCR testify to a capacity to no produce infective recombinant viruses determined by specific PCR of the expected fragment of the genomic DNA of NIH3T3 cells. The production of retroviruses at a significant titre in two clones was demonstrated.

The infective retrovirus clone F6 ($5\times10^4$) produces a retrovirus with the complete region of the signal sequence (4 repeats of the whole L4L3 fragments (see FIG. 3)), and the clone B8 ($2\times10^5$) with a partially deleted signal sequence (a single whole L4L3 motif and a small portion of the L3 cassette of a second motif (see FIG. 3)).

The titres of retroviruses were estimated by semi-quantitative PCR-RT using different deletions in pHSG (L4L3)4199PKCAT as standards.

EXAMPLE 5
Infection With a Recombinant Retrovirus, Estimation of the Titre of Retrovirus and Assay of the CAT Protein The positive clones are used to infect NIH3T3 cells in order to estimate the infective capacities of the retroviruses produced.

1 ml of cell culture supernatant at 100% confluence is used to infect NIH3T3 cells in logarithmic growth with 8 $\mu$g/ml of polybrene. After 3 hours of incubation, the polybrene is diluted to 2 $\mu$g/ml with medium, and culturing is continued for 48 hours. The genomic DNA of the infected NIH3T3 cells is extracted and used for a PCR amplification, employing the probes described in Example 3. Detection of the specific amplified fragment proves the integration of the retroviral sequences in the genome of the infected cells. Their titre is estimated by comparing the intensities of the amplified DNA bands originating from the genomic DNA of the infected cells with bands originating from different dilutions of the retrovirus ($10^2$ to $10^6$ molecules). Clones which produce infective retroviruses are cocultured with mhATIIIF cells according to the following protocol:

A 60-mm well whose base has been removed and whose walls have been coated with silicone oil is placed inside a 90-mm well so as to divide it into two parts.

mhATIIIF cells and cells producing the retrovirus are introduced into it in the centre and at the periphery, respectively, taking care not to mix the two types of cells.

When the cells are well attached to the wells after 6 hours of incubation, the small well is removed. The medium is changed for a further incubation of 16 hours, polybrene is then added (8 $\mu$g) and the cells are cultured for 48 hours.

The CAT activity is measured by thin-layer chromatography and quantified in cpm by scintillation.

EXAMPLE 6
Induction With Glucose at Different Doses and Times of the Expression of the Chimera The mhATIIIF cell line, which may be likened to the hepatocytes in rats, retains its capacity to respond to glucose by transcriptional activation of the L-PK gene, and is hence suitable for testing the response of the CAT transgene transferred by the retroviral vector, and consequently the activity of the GIRE L-PK in a retroviral environment.

Figure 4:
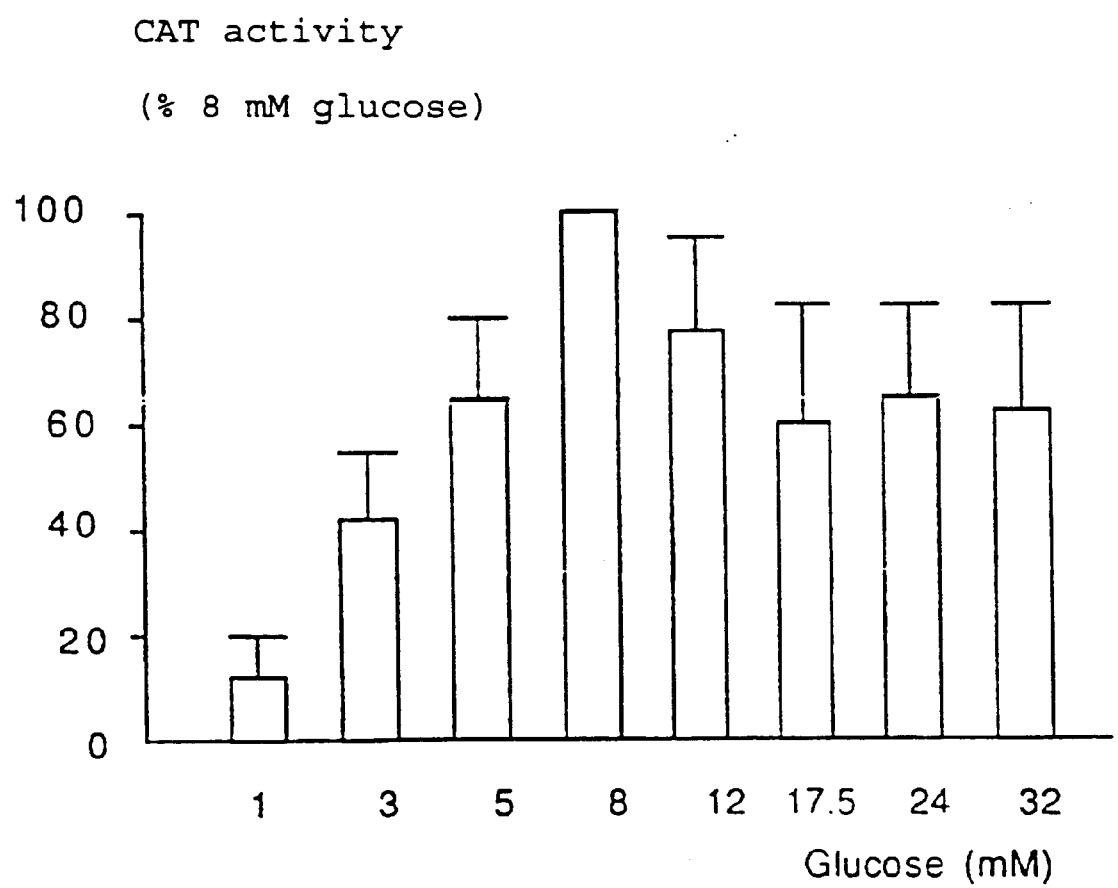
FIG. 4: Quantitative determination of the CAT activity in mhATIIIF cells transformed with the clone B8, as a function of the amount of glucose injected.
Figure 5:
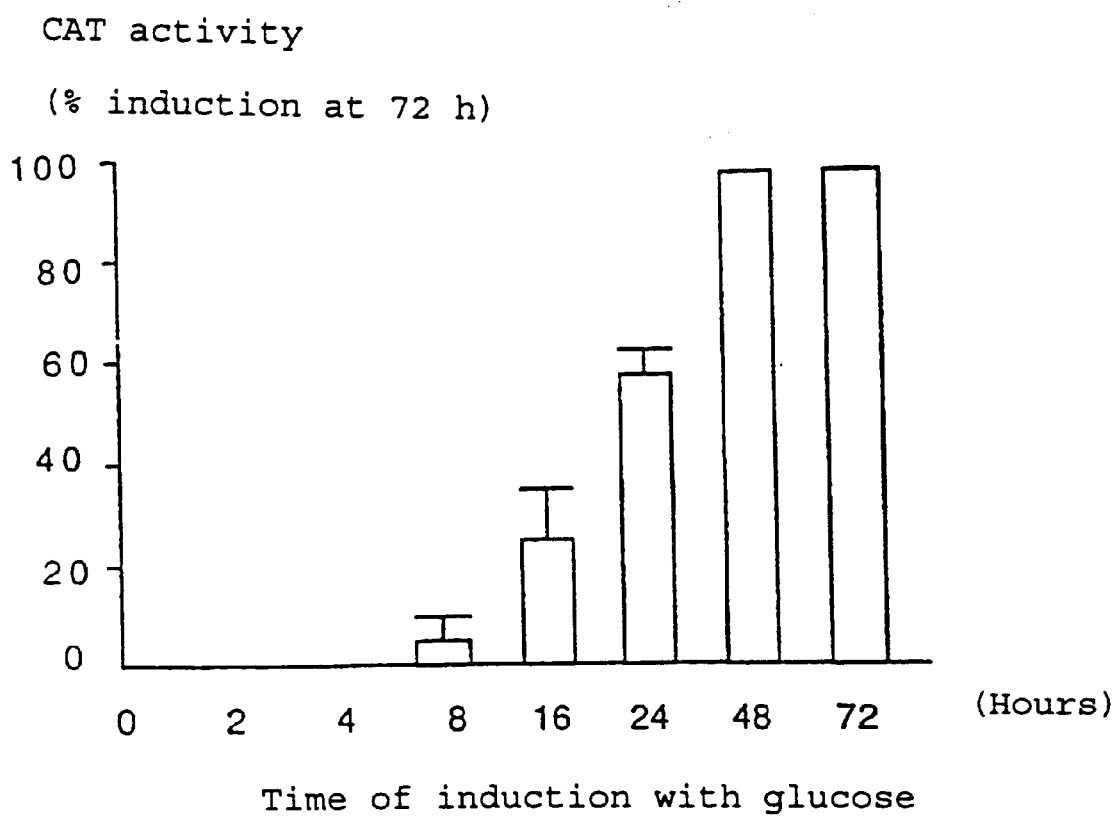
FIG. 5: Quantitative determination of the CAT activity in mhATIIIF cells transformed with the clone B8 at different induction times.

To increase the efficacy of the transfection, the mhATIIIF cells are cultured twice with cells producing retroviruses, leading to a satisfactory degree of infection with the clone B8. As shown in FIGS. 4 and 5, expression of the L-PK/CAT transgene in the infected mhATIIIF cells is indeed induced by glucose, with half the maximal induction obtained for 3–4 mM glucose and maximal induction for 8 mM glucose. For higher glucose concentrations, the CAT activity remains relatively stable.

The mhATIIIF cells are cultured in a medium containing 17 mM glucose, induction of the gene is observed from the 8th hour of incubation, induction to one half before the 24th hour and maximal induction at the 48th hour.

EXAMPLE 7
Construction of the plasmids pHSG/PK-CAT and pHSG/AL-PK-CAT

Figure 6:
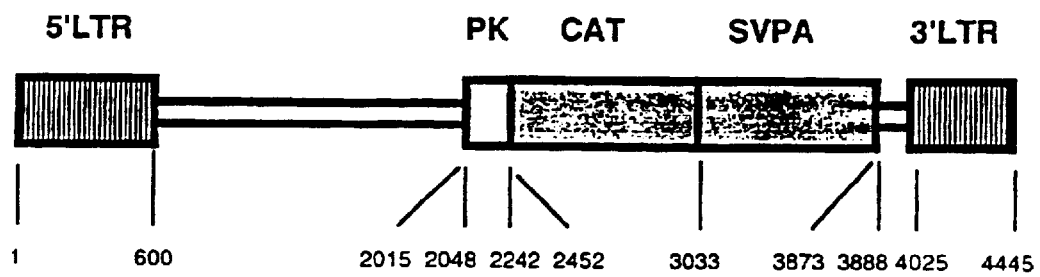
FIG. 6: Construction of the plasmids pHSG/PK-CAT and pHSG/AL-PK-CAT.
Figure 6:
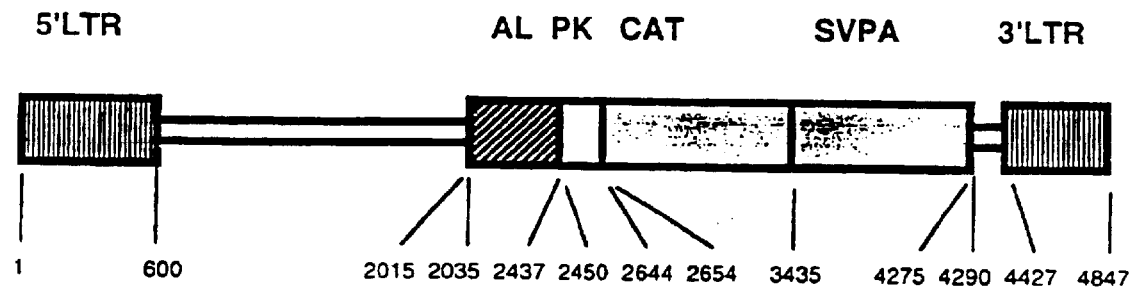

The plasmids are constructed according to standard DNA cloning techniques. The junctions are checked by DNA sequencing. The plasmid construct pHSG/PK-CAT contains the MMLV part of pHSG situated between nucleotides 1 to 2015 and 3888 to 4445; for the plasmid pHSG/AL-PK-CAT, the MMLV sequences are situated between nucleotides 1 to 2015 and 4290 to 4847 (FIG. 6). The sequence which codes for the CAT gene under the control of the rat L-type pyruvate kinase gene promoter (−183 to +11 bp) is situated between nucleotides 2048 and 3033 for the plasmid pHSG/PK-CAT and between 2450 and 3435 for the plasmid pHSG/AL-PK-CAT. The sequence of the enhancer fragment of the aldolase B gene (SEQ ID NO: 6) is situated between nucleotides 2035 and 2437 in the plasmid pHSG/AL-PK-CAT. The poly A signal sequence used is that from SV40, situated between nucleotides 3033 and 3873 in pHSG/PR-CAT and between 3435 and 4275 in pHSG/AL-PK-CAT. Nucleotides 2015 to 2048; 2242 to 2452 and 3873 to 3888 are adaptors between the different fragments for the plasmid pHSG/PK-CAT; they are situated for the plasmid pHSG/AL-PK-CAT from 2015 to 2035; 2437 to 2450; 2644 to 2654 and 4275 to 4290.

Figure 7:
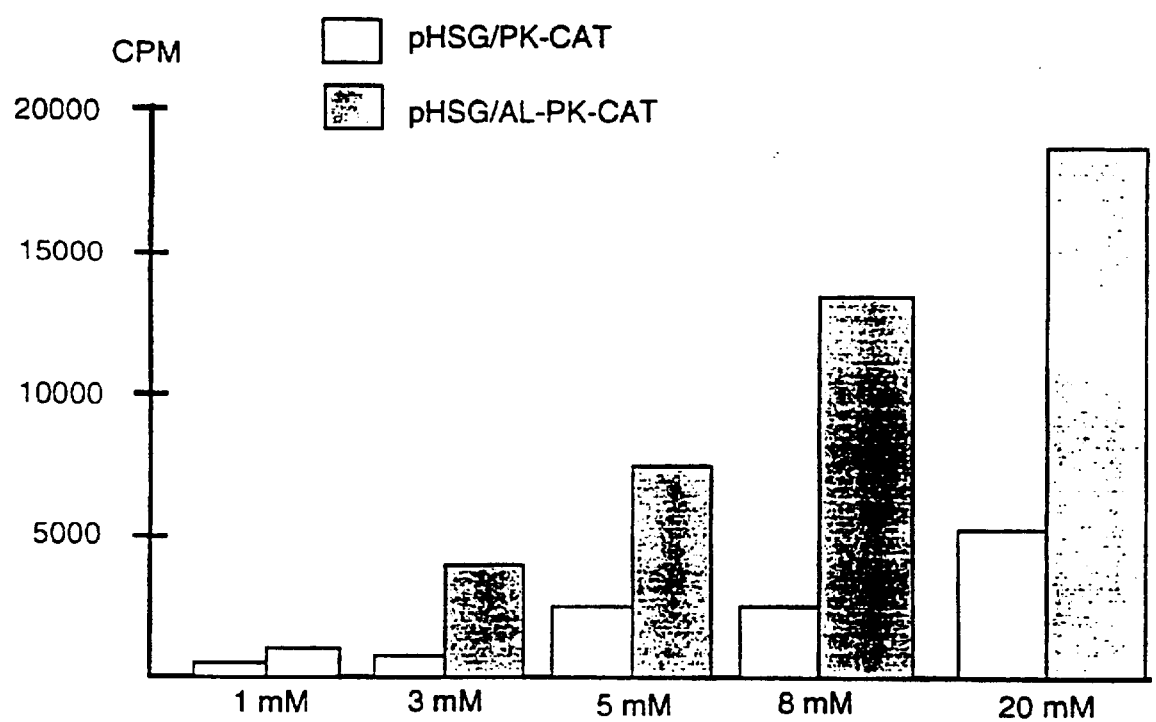
FIG. 7: Induction, by a glucose at different doses, of the expression of the plasmids pHSG/PK-CAT and pHSG/AL-PK-CAT.

EXAMPLE 8
Induction, by Glucose at Different Doses, of the Expression of the Plasmids pHSG/PK-CAT and pHSG/AL-PK-CAT The cell line mhAT3F is derived from a liver tumour in a transgenic mouse expressing the SV40 early genes under the control of the antithrombin III promoter specific for the liver (Kahn A. et. al. Exp; Cell. Res; 200, 175–185). These cells were cultured at 37° C. with 5% (vol/vol) $CO_2$ in a DMEM F12/NUT.MIX nutrient medium (1:1 vol/vol) with glutamax-1 (Gibco-BRL) with or without D-glucose (Sigma), supplemented with 1 μM dexamethasone, 1 μM triodothyronine and 20 nM human insulin. 5 μg of the plasmid pHSG/PK-CAT or of the plasmid pHSG/AL-PK-CAT were transfected by the cationic liposome method (DOPAP, Boehringer Mannheim). The cells were subsequently cultured in the presence of different concentrations of glucose for 24 hours in order to induce the PK-L promoter. The CAT activity is measured by thin-layer chromatography and quantified in cpm by scintillation. The result are presented in FIG. 7. After 24 hours 6of induction in the presence of different concentrations of glucose, the expression of the plasmid pHSG/PK-L in the presence of the aldolase B enhancer is 5↑ times higher in the presence of 8 mM glucose than that of the plasmid lacking the aldolase B enhancer (FIG. 7).

This aldolase B/PK-L hybrid promoter is therefore particularly advantageous for conferring on a gene a high level of expression while remaining sensitive to glucose, especially in the context of the development of a gene therapy method for diabetes which are intended to produce, according to the glycaemia, an appropriate concentration of insulin in vivo.

What is claimed is:

1. A replication defective recombinant virus comprising at least one heterologous gene under the control of an expression signal, wherein the expression signal comprises a glucose-responsive L pyruvate kinase (L-PK) gene promoter sequence.

2. The replication defective recombinant virus according to claim 1, wherein the signal sequence comprises 183 base pairs located at the '5 end of the L-PK gene.

3. The replication defective recombinant virus according to claim 1, wherein the expression signal comprises all or part of the L4 element in SEQ ID NO: 1.

4. A replication defective recombinant virus comprising at least one heterologous gene under the control of an expression signal, wherein the expression signal comprises an L4 element of a promoter of an L-PK gene.

5. The replication defective recombinant virus according to claim 4, wherein the L4 element comprises SEQ ID NO: 2, or a sequence that hybridizes with SEQ ID NO: 2 and interacts with factor MLTF/USF.

6. The replication defective recombinant virus according to claim 4, wherein the L4 element is present as four consecutive repeats.

7. The replication defective recombinant virus according to claim 4, further comprising an L3 element of the promoter of the L-PK gene.

8. The replication defective recombinant virus according to claim 7, wherein the L3 element comprises SEQ ID NO: 3, or a sequence that hybridizes with SEQ ID NO: 3 and interacts with factor HNF4.

9. The replication defective recombinant virus according to claim 1, wherein the expression signal comprises an L4-L3 oligomer comprising an L4 element of the promoter of the L-PK gene fused upstream of an L3 element of the promoter of the L-PK gene.

10. The replication defective recombinant virus according to claim 9, wherein the expression signal comprises four successive L4-L3 oligomers.

11. The replication defective recombinant virus according to claim 1, wherein the expression signal further comprises a minimal promoter.

12. The replication defective recombinant virus according to claim 11, wherein the promoter comprises base pairs -119 to 11 located at the 5' end of the L-PK gene.

13. The replication defective recombinant virus according to claim 1, wherein the expression signal comprises SEQ ID NO: 4, or a derivative thereof.

14. The replication defective recombinant virus according to claim 1, wherein the expression signal further comprises a transcriptional enhancer.

15. The replication defective recombinant virus according to claim 14, wherein the transcriptional enhancer comprises a first intron of a rat aldolase B gene.

16. The replication defective recombinant virus according to claim 1, wherein said virus has a genome lacking at least one region necessary for replication in a target cell.

17. The replication defective recombinant virus according to claim 1, wherein the virus is an adenovirus.

18. The replication defective recombinant virus according to claim 17, wherein the adenovirus is selected from a group consisting of human adenovirus type Ad 2, human adenovirus type Ad 5, and canine adenovirus type CAV-2.

19. The replication defective recombinant virus according to claim 1, wherein the virus is a retrovirus.

20. The replication defective recombinant virus according to claim 19, wherein the retrovirus is a MoMuLV family retrovirus.

21. The replication defective recombinant virus according to claim 1, wherein the heterologous gene encodes insulin or a variant thereof.

22. An isolated mammalian cell infected with at least one replication defective recombinant virus according to claim 1.

23. The isolated mammalian cell according to claim 22, wherein said cell is a human cell.

24. The isolated mammalian cell according to claim 23, wherein said cell is a hepatocyte of a pancreatic β cell.

* * * * *